US008101795B2

(12) United States Patent
Yoshida et al.

(10) Patent No.: US 8,101,795 B2
(45) Date of Patent: Jan. 24, 2012

(54) PROCESS FOR PREPARING HIGH PURITY COROSOLIC ACID AND HIGH PURITY URSOLIC ACID

(75) Inventors: Naoaki Yoshida, Tokyo-To (JP); Chihiro Mori, Yotsukaido (JP); Tsutomu Sasaki, Sosa (JP)

(73) Assignees: Kenko Corporation, Tokyo-To (JP); Tokiwa Phytochemical Co., Ltd., Chiba-Ken (JP)

( * ) Notice: Subject to any disclaimer, the term of this patent is extended or adjusted under 35 U.S.C. 154(b) by 1028 days.

(21) Appl. No.: 12/005,343

(22) Filed: Dec. 27, 2007

(65) Prior Publication Data

US 2009/0275778 A1   Nov. 5, 2009

(30) Foreign Application Priority Data

Apr. 4, 2007   (JP) .................................. 2007-121954

(51) Int. Cl.
*C07C 61/28* (2006.01)
*A61K 31/20* (2006.01)

(52) U.S. Cl. ........................................ 562/498; 514/559
(58) Field of Classification Search .................... None
See application file for complete search history.

(56) References Cited

U.S. PATENT DOCUMENTS

| 6,908,632 | B1 | 6/2005 | Zhao et al. | |
| 2005/0137259 | A1 | 6/2005 | Matsuyama et al. | |
| 2005/0143464 | A1* | 6/2005 | Matsuyama et al. | .......... 514/559 |
| 2005/0255569 | A1 | 11/2005 | Matsuyama et al. | |
| 2005/0267055 | A1 | 12/2005 | Matsuyama et al. | |
| 2006/0235078 | A1 | 10/2006 | Matsuyama et al. | |
| 2007/0093552 | A1 | 4/2007 | Matsuyama et al. | |

FOREIGN PATENT DOCUMENTS

| CN | 1629180 | * | 6/2005 |
| EP | 1 702 615 | | 9/2006 |
| JP | 09-143050 | | 6/1997 |
| JP | 2002-255781 | | 9/2002 |
| JP | 2002-345434 | | 12/2002 |
| JP | 2005-263650 | | 9/2005 |
| WO | 2006/090613 | | 8/2006 |

OTHER PUBLICATIONS

Murakami, C. et al., Screening of Plant Constituents for Effect on Glucose Transport Activity in Ehrlich Ascites Tumour Cells, *Chem. Pharm. Bull.*, vol. 41, No. 12 (1993), pp. 2129-2131.

De Tommast, N. et al., Hypoglycemic Effects of Sesquiterpene Glycosides and Polyhydroxylated Triterpenoids of *Eriobotrya japonica*, Planta Med., vol. 57 (1991), pp. 414-416.
Li, J. et al., Effects of ursolic acid and oleanolic acid on human colon carcinoma cell line HCT15, *World J Gastroenterol*, vol. 8, No. 3 (2002), pp. 493-495.
Tian, Z. et al., Anti-hepatoma activity and mechanism of ursolic acid and its derivatives isolated from *Aralia decaisneana*, World J Gastroenterol, vol. 12, No. 6 (Feb. 14, 2006), pp. 874-879.
Hirai, Masashi, *Purification and Characteristcs of Sorbitol-6-phosphate Dehydroqenase from Loquat Leaves*, Plant Physiol. (1981), vol. 67, pp. 221-224.
Shimizu, Mineo et al., *Anti-inflammatory Constituents of Topically Applied Crude Drugs I. Constituents and Anti-inflammatory Effect of Eriobotrya japonica LINDL*, Chem. Pharm. Bull. (1986), vol. 34(6), pp. 2614-2617.
De Tommasi, Nunziatina et al., *Hypoglycemic Effects of Sesquiterpene Glycosides and Polyhydroxylated Triterpenoids of Eriobotrya japonica*, Planta Med. (1991), vol. 57, pp. 414-416.
Nishioka et al., *Effects of Extract Derived from Eriobotrya japonica on Liver Function Improvement in Rats*, Biol. Pharm. Bull. (2002), vol. 25 No. 8, pp. 1053-1057.
Kawahara, Nobuo et al., *A New Acylated Flavonol Glycoside from the Leaves of Eriobotrya japonica*, Chem. Pharm. Bull. (2002), vol. 50 No. 12, pp. 1619-1620.
Taniguchi, Shoko, *Effective Productions of Plant Secondary Metabolites Having Antitumor Activity by Plant Cell and Tissue Cultures*, Yakugaku Zasshi (2005), vol. 125 No. 6, pp. 499-507.
Banno, Norihiro et al., *Anti-inflammatory and Antitumor-Promotinq Effects of the Triterpene Acids from the Leaves of Erobotrya japonica*, Biol. Pharm. Bull. (2005), vol. 28 No. 10, pp. 1995-1999.
Young, Han-Suk et al., *Antitumor Effects of Ursolic Acid Isolated from the Leaves of Eriobotrya joponica*, Natural Medicines (1995), vol. 49 No. 2, pp. 190-192.
Liang, Zhou Zhoug et al., *Polyhydroxylated Triterpens from Eriobotrya japonica*, Planta Med. (1990), vol. 56, pp. 330-332.
Database WPI Week 200571, Thomson Scientific, London, GB; AN 2005-684323 (XP002491994), abstract of CN 1 629 180 A (Yang Q), Jun. 22, 2005.
Database WPI Week 200526, Thompson Scientific, London, GB; AN 2005-243255 (XP002491995), abstract of CN 1 557 832 A (Zhang S), Dec. 29, 2004.

* cited by examiner

*Primary Examiner* — Daniel Sullivan
*Assistant Examiner* — Yevegeny Valenrod
(74) *Attorney, Agent, or Firm* — Wenderoth, Lind & Ponack, L.L.P.

(57) ABSTRACT

According to the present invention, there is provided a process for preparing corosolic acid comprising the steps of (1) dissolving crude extract of Japanese loquat leaves in alkali and aqueous alcohol and (2) applying the solution to a nonpolar adsorption resin to obtain corosolic acid.

16 Claims, No Drawings

PROCESS FOR PREPARING HIGH PURITY COROSOLIC ACID AND HIGH PURITY URSOLIC ACID

BACKGROUND OF THE INVENTION

1. Technical Field

The present invention relates to a process for preparing high purity corosolic acid and high purity ursolic acid.

2. Background Art

Corosolic acid is known to have insulin-like activity (Chem. Pharm. Bull. (1993) 41(12): 2129-2131), to help sugar uptake into cells (Chem. Pharm. Bull. (1993) 41(12): 2129-2131), to have an effect of suppressing elevation of blood glucose level (Planta Med. (1991) 57: 414-416), and the like. Ursolic acid is known to prevent generation of wrinkles (Japanese Patent Laid-open Publication No. H09-143050), to improve fascicular degradation due to ultraviolet rays (Japanese Patent Laid-open Publication No. 2002-255781), to have an antitumor effect (World J Gastroenterol (2002) 8(3): 493-495, World J Gastroenterol (2006) 12(6): 874-879), and the like. Since corosolic acid and ursolic acid have been confirmed to have various effects, respectively, as described above, manufacturing of high purity corosolic acid and high purity ursolic acid has been desired.

As for corosolic acid, a production method of extracting Banaba leaves with hydrous ethanol, treating the extract with activated carbon, then concentrating the extract, and collecting the precipitates (Japanese Patent Laid-open Publication No. 2005-263650); a method of preparing an extract containing corosolic acid from loquat leaves (U.S. Pat. No. 6,908,632), and the like have been disclosed. As for ursolic acid, a method of obtaining a mixed concentrate of ursolic acid and an oleanolic acid derivative (Japanese Patent Laid-open Publication No. 2002-345434), and the like have been disclosed.

Japanese loquat (Scientific name: *Eriobotrya japonica*; English name: Japanese loquat, Japanese medlar, Japanese plum, Japanese name: Biwa) is an evergreen low fruit tree with a height of 3 to 8 m, and widely distributed in China and Japan. The leaves are oblong with a length of 15 to 30 cm and a width of 3 to 7 cm, and are thick and hard. The leaves are glossy dark green and alternate. In China, the leaves are used for antimicrobial, antitussive, expectorant, diuretic purposes and the alleviation of heat exhaustion. Also, a compress containing infusion of the leaves is used for the alleviation of skin diseases. The leaves are known to contain several triterpene compounds including ursolic acid, oleanolic acid, corosolic acid, and maslic acid (U.S. Patent Application Publication No. 2005/0137259).

However, a process for preparing high purity corosolic acid and high purity ursolic acid using Japanese loquat leaves as a raw material which can be conducted efficiently and under such conditions that corosolic acid and high purity ursolic acid are useful as foods has not been disclosed.

SUMMARY OF THE INVENTION

The present inventors have found that high purity corosolic acid and high purity ursolic acid can be prepared efficiently by treating crude extract of Japanese loquat leaves with alkali and aqueous alcohol, and performing separation and purification using an adsorption resin. The present invention is based on this finding.

An object of the present invention is to prepare high purity corosolic acid and high purity ursolic acid efficiently using Japanese loquat leaves as a raw material.

According to the present invention, there is provided a process for preparing corosolic acid comprising the steps of:
(1) dissolving crude extract of Japanese loquat leaves in alkali and aqueous alcohol; and
(2) applying the solution to a nonpolar adsorption resin to obtain corosolic acid.

According to the present invention, there is further provided a process for preparing ursolic acid comprising the steps of:
(1') dissolving crude extract of Japanese loquat leaves in alkali and aqueous alcohol; and
(2') applying the solution to a nonpolar adsorption resin to obtain ursolic acid.

The preparation process according to the present invention is advantageous in that high purity corosolic acid and high purity ursolic acid can be prepared efficiently. The preparation process according to the present invention is also advantageous in that high purity corosolic acid and high purity ursolic acid can be stably supplied at a low cost using Japanese loquat leaves widely cultivated for foods as a raw material.

Since both corosolic acid and ursolic acid obtained by the preparation process according to the present invention are of high purity respectively, the process of the present invention is advantageous in that the compounds can be utilized for pharmaceuticals, quasi drugs, cosmetics, and the like for the purpose of exerting the known effects of the respective compounds and that the compounds can be used as food materials by limiting a solvent to be used to ethanol.

DETAILED DESCRIPTION OF THE INVENTION

The present invention will be explained in more details as follows. The following description is presented for the purpose of illustrating the present invention and is not intended to limit the invention to the described embodiments only. The present invention can be carried out in various forms as long as they do not depart from the spirit and scope of the invention.

Prior art literature and patent literature such as Patent Application Publication Gazette cited in the present specification are all incorporated into this specification by reference and can be used to carry out the present invention.

Crude Extract

A crude extract can be prepared from a crude extract liquid obtained by extracting Japanese loquat leaves according to a known method. Specifically, a crude extract can be obtained by extracting Japanese loquat leaves with a lower alcohol, and then reducing the alcohol concentration of the crude extract liquid.

Japanese loquat leaves (*Eriobotrya japonica*) used as a raw material in the present invention can be freshly collected without any processing or dried before extraction operation. The drying method includes known methods such as lyophilization, solar drying, and hot air drying. It is preferable that leaves should be dried and finely crushed in terms of extraction efficiency.

The solvent used for extraction includes lower alcohols, preferably methanol or ethanol.

The alcohol content of the lower alcohol is preferably 80 to 99.5% by volume, more preferably 99.5%.

The extraction operation can be carried out, for example, by extraction while heating and stirring, by immersion of Japanese loquat leaves in a solvent (cold extraction or warm extraction), and the like.

As for the extraction conditions, the extraction temperature is preferably 60° C. or higher to the boiling point or lower. A reflux apparatus to prevent evaporation of alcohol and a stirrer to increase extraction efficiency, and the like can be provided in the extraction equipment. Further, treatment with activated carbon can be conducted to increase the purity of a crude extract liquid.

The crude extract can be obtained by collecting insoluble generated by decreasing the alcohol concentration of the crude extract liquid thus obtained. The crude extract has a corosolic acid content of 7 to 15% by weight and an ursolic acid content of 7 to 15% by weight.

Examples of the method of decreasing the alcohol concentration of the crude extract liquid include addition of water and concentration (for example, concentration under reduced pressure).

In order to obtain the crude extract, the alcohol concentration can be decreased to 65% by weight or lower, preferably 50% by weight or lower.

The method of collecting insoluble is preferably filtration or centrifugation. When filtration performance is poor, a filter aid can be used.

Dissolution Step

A crude extract-dissolved solution can be obtained by adding alkali and aqueous alcohol solution to the crude extract obtained.

The alkali can be used in a sufficient amount to make the pH of the aqueous alcohol at pH 11 to pH 14. For example, the alkali can be added in an amount of 0.05 to 0.5 g with respect to 1 g of the crude extract, or added in an amount of 0.5 to 5 g with respect to 100 ml of the aqueous alcohol.

Examples of the alkali include alkaline metal hydroxides, preferably sodium hydroxide or potassium hydroxide.

The alkali can be added as it is or used after dissolving it in the aqueous alcohol.

The alcohol for the aqueous alcohol used to dissolve the crude extract can be, for example, methanol, ethanol and the like.

The alcohol content of the aqueous alcohol is preferably 40 to 70% by volume, more preferably 50 to 60% by volume.

Separation and Purification Step

Corosolic acid and ursolic acid can be obtained by applying the solution thus obtained to a nonpolar adsorption resin. Specifically, the solution obtained is applied to a container filled with a nonpolar adsorption resin followed by development with alcohol for development to fractionate the solution to obtain corosolic acid, and then a high concentration alcohol is flown after the fractionation to obtain ursolic acid.

According to the process for preparing corosolic acid of the present invention, corosolic acid can be obtained by applying the solution obtained to a container filled with a nonpolar adsorption resin followed by development with alcohol for development to fractionate the solution, and then collecting corosolic acid fractions using the result of HPLC analysis as an index. High purity corosolic acid (with a content of 15 to 600% by weight) can be obtained by acidifying the collected fractions with an acid and drying the precipitated crystals. Alternatively, higher purity corosolic acid (with a content of 60 to 900% by weight) can be obtained by applying the solution obtained to a container filled with a nonpolar adsorption resin followed by development with alcohol for development to fractionate the solution, and then collecting fractions having particularly high corosolic acid concentrations (concentrated corosolic acid fractions) using the result of HPLC analysis as an index, acidifying the fractions with an acid, and drying the precipitated crystals.

According to the process for preparing ursolic acid of the present invention, ursolic acid can be obtained by applying the solution obtained to a container filled with a nonpolar adsorption resin followed by development with alcohol for development, and then flowing alcohol for elution that has a higher alcohol concentration than the alcohol for development, and collecting the alcohol for elution. High purity ursolic acid (with a content of 15 to 90% by weight) can be obtained by acidifying the collected alcohol for elution with an acid and drying the precipitated crystals.

The nonpolar adsorption resin can be, for example, styrene-divinylbenzene or acryl-divinylbenzene synthetic adsorption resins, preferably HP20, XAD4, and the like.

The container to be filled with a nonpolar adsorption resin can be, for example, a column, and the like.

The alcohol for development can be, for example, methanol, ethanol, and the like.

The alcohol content of the alcohol for development is preferably 40 to 70% by volume, more preferably 50 to 60% by volume.

The conditions of fractionation through a nonpolar adsorption resin can be appropriately determined by those skilled in the art. For example, when the solution obtained is applied to a container filled with a nonpolar adsorption resin followed by development with alcohol for development to be fractionated into 20 fractions (Fraction 1 to Fraction 20), Fraction 7 to Fraction 12 can be collected as corosolic acid fractions and Fraction 10 can be collected as a high concentration corosolic acid fraction.

The HPLC analysis conditions can be appropriately determined by those skilled in the art. Further, those skilled in the art can select corosolic acid fractions using the result of HPLC analysis as an index.

The alcohol used as the alcohol for elution can be, for example, methanol, ethanol, and the like.

Although the alcohol content of the alcohol for elution can be satisfactory as long as it is higher than that of the alcohol for development, it is preferably 80 to 99.5% by volume, more preferably 99.5% by volume.

The acid used for precipitation of corosolic acid and ursolic acid can be any as long as the acid can make pH of the solution obtained at 1 to 4, and includes hydrochloric acid and sulfuric acid, preferably hydrochloric acid.

A preferred embodiment of the process for preparing corosolic acid according to the present invention is a process for preparing corosolic acid comprising the steps of (1) extracting Japanese loquat leaves with 80 to 99.5% by volume lower alcohol followed by concentration under reduced pressure to obtain crude extract, and dissolving the crude extract in sodium hydroxide or potassium hydroxide and 40 to 70% by volume aqueous alcohol; and (2) applying the solution to a column filled with HP20, developing the column with alcohol for development, and collecting corosolic acid fractions using the result of HPLC analysis as an index.

A preferred embodiment of the process for preparing corosolic acid according to the present invention is a process for preparing corosolic acid comprising the steps of (1) extracting Japanese loquat leaves with 80 to 99.5% by volume lower alcohol followed by concentration under reduced pressure to obtain crude extract, and dissolving the crude extract in sodium hydroxide or potassium hydroxide and 40 to 70% by volume aqueous alcohol; and (2) applying the solution to a column filled with HP20, developing the column with alcohol for development, and collecting concentrated corosolic acid fractions using the result of HPLC analysis as an index.

A preferred embodiment of the process for preparing ursolic acid according to the present invention is a process for preparing ursolic acid comprising the steps of (1') extracting Japanese loquat leaves with 80 to 99.5% by volume lower alcohol followed by concentration under reduced pressure to obtain crude extract, and dissolving the crude extract in sodium hydroxide or potassium hydroxide and 40 to 70% by volume aqueous alcohol; and (2') applying the solution to a column filled with HP20, developing the column with alcohol for development, then flowing 80 to 99.5% by volume alcohol for elution, and collecting the alcohol for elution.

According to the present invention, leaves other than Japanese loquat leaves can be used as long as high purity corosolic acid can be prepared efficiently and leaves of Banaba can be used instead of Japanese loquat leaves.

According to the present invention, leaves other than Japanese loquat leaves can be used as long as high purity ursolic acid can be prepared efficiently and leaves of uva ursi or rosemary can be used instead of Japanese loquat leaves.

EXAMPLES

Example 1

Preparation of Crude Extract

Dried Japanese loquat leaves (produced in China) were crushed and 10 L of 99.5% by volume methanol (manufactured by Kanto Chemical Co., Inc.) was added to 1 kg of the crushed material thus obtained. Extraction was conducted while heating under reflux followed by filtration to obtain crude extract liquid. These operations were repeated twice, and crude extract liquids thus obtained were combined. Activated carbon was added to the combined crude extract liquid to adsorb and remove chlorophylls. This liquid was then concentrated to 2 L under reduced pressure. One liter of warm water was added while stirring and the resultant mixture was left standing. Light yellow insoluble generated was collected by filtration. The collection was dried to obtain crude extract (38.5 g). The contents of corosolic acid and ursolic acid in the crude extract were measured using HPLC (manufactured by Waters Corporation), respectively. The corosolic acid content was 12.4% by weight and the ursolic acid content was 13.3% by weight.

Example 2

Separation and Purification of Corosolic Acid and Ursolic Acid

To 10 g of the crude extract obtained in Example 1, 100 mL of 50% by volume methanol (manufactured by Kanto Chemical Co., Inc.) and 2 g of sodium hydroxide were added. After dissolution by stirring, insoluble was removed by filtration and a filtrate was obtained. The insoluble was washed with 15 mL of water by stirring and filtered off. The washing liquid was combined with the filtrate. This liquid was applied to a column filled with 200 mL of HP20 (manufactured by Mitsubishi Chemical Corporation) and the column was developed with 50% by volume methanol to obtain 100 mL fractions. Each fraction was analyzed by HPLC. The operating condition of HPLC was as follows.
Detector: UV absorptiometer (wavelength for measurement: 210 nm)
Column: A column filled with octadecylsilyl silica gel for liquid chromatography
Mobile phase: A mixture of acetonitrile and 0.1% trifluoroacetic acid solution (65:35)
Temperature: 40° C.
Flow rate: Adjusted so that the retention time of corosolic acid is about 10 minutes (1.0 to 1.5 mL/min)

When the corosolic acid content was high, the HPLC area was measured after optionally diluted with methanol.

The results confirmed that ingredients other than corosolic acid and ursolic acid were eluted in Fractions 1 to 6, and that corosolic acid was mainly eluted in Fractions 7 to 12 (Table 1).

TABLE 1

Area of peak corresponding to corosolic acid in HPLC analysis

| Fraction No. | HPLC area |
|---|---|
| 1 | 0 |
| 2 | 0 |
| 3 | 0 |
| 4 | 0 |
| 5 | 1654 |
| 6 | 2123 |
| 7 | 29878 |
| 8 | 59878 |
| 9 | 287899 |
| 10 | 549878 |
| 11 | 213432 |
| 12 | 61284 |
| 13 | 7323 |
| 14 | 5323 |
| 15 | 3009 |
| 16 | 2899 |
| 17 | 1998 |
| 18 | 1011 |
| 19 | 765 |
| 20 | 594 |

The values in the table were corrected by the dilution rate.

Next, 99.5% by volume methanol was flown to collect ursolic acid and wash the resin.

Fractions 7 to 12 obtained were acidified with 5 N hydrochloric acid to pH 2.5 and precipitated crystals were dried. As a result, 2.7 g of corosolic acid having a content of 32% by weight was obtained (measured by HPLC).

After water was added to the 99.5% by volume methanol part, the resultant mixture was acidified with hydrochloric acid to pH 2.5 and precipitated crystals were dried. As a result, 1.1 g high purity ursolic acid having a content of 75% by weight was obtained (measured by HPLC).

Example 3

Separation and Purification of Corosolic Acid

Fraction 10 alone among Fractions 7 to 12 obtained in Example 2 was acidified with 5 N hydrochloric acid to pH 2.5 and precipitated crystals were dried. As a result, 1.0 g of high purity corosolic acid having a content of 75% by weight was obtained (measured by HPLC).

What is claimed is:

1. A process for preparing corosolic acid comprising the steps of:
   (1) dissolving crude extract of Japanese loquat leaves in alkali and aqueous alcohol to form a solution; and
   (2) applying the solution to a nonpolar adsorption resin to obtain corosolic acid.

2. The process according to claim 1, wherein step (2) comprises the steps of applying the solution to a nonpolar adsorption resin followed by development with alcohol for development, and collecting corosolic acid fractions.

3. The process according to claim 1, wherein the alkali is an alkaline metal hydroxide.

4. The process according to claim 3, wherein the alkaline metal hydroxide is sodium hydroxide or potassium hydroxide.

5. The process according to claim 1, wherein the alcohol content of the aqueous alcohol in step (1) is 40 to 70% by volume.

6. The process according to claim 1, wherein the alcohol in step (1) is methanol or ethanol.

7. The process according to claim 1, wherein the nonpolar adsorption resin is a styrene-divinylbenzene resin or an acryl-divinylbenzene resin.

8. The process according to claim 1, wherein the nonpolar adsorption resin is HP 20 or XAD4.

9. A process for preparing ursolic acid comprising the following steps:
 (1') dissolving crude extract of Japanese loquat leaves in alkali and aqueous alcohol to form a solution; and
 (2') applying the solution to a nonpolar adsorption resin to obtain ursolic acid.

10. The process according to claim 9, wherein step (2') comprises the step of applying the solution to a nonpolar adsorption resin followed by development with alcohol for development, then flowing alcohol that has a higher concentration than the alcohol for development, and collecting the high concentration alcohol.

11. The process according to claim 9, wherein the alkali is an alkaline metal hydroxide.

12. The process according to claim 11, wherein the alkaline metal hydroxide is sodium hydroxide or potassium hydroxide.

13. The process according to claim 9, wherein the alcohol content of the aqueous alcohol in step (1') is 40 to 70% by volume.

14. The process according to claim 9, wherein the alcohol in step (1') is methanol or ethanol.

15. The process according to claim 9, wherein the nonpolar adsorption resin is a styrene-divinylbenzene resin or an acryl-divinylbenzene resin.

16. The process according to claim 9, wherein the nonpolar adsorption resin is HP 20 or XAD4.

* * * * *